United States Patent
Sun

(10) Patent No.: US 12,180,132 B2
(45) Date of Patent: Dec. 31, 2024

(54) COMPOSITIONS AND METHODS FOR SYNTHESIS OF 2,3-DICHLORO-1,1,1,2-TETRAFLUORO-PROPANE AND 2,3,3,3-TETRAFLUOROPROPENE

(71) Applicant: THE CHEMOURS COMPANY FC, LLC, Wilmington, DE (US)

(72) Inventor: Xuehui Sun, Kennett Square, PA (US)

(73) Assignee: THE CHEMOURS COMPANY FC, LLC, Wilmington, DE (US)

( * ) Notice: Subject to any disclaimer, the term of this patent is extended or adjusted under 35 U.S.C. 154(b) by 371 days.

(21) Appl. No.: 17/619,388

(22) PCT Filed: Jul. 1, 2020

(86) PCT No.: PCT/US2020/040403
§ 371 (c)(1),
(2) Date: Dec. 15, 2021

(87) PCT Pub. No.: WO2021/003207
PCT Pub. Date: Jan. 7, 2021

(65) Prior Publication Data
US 2022/0306557 A1  Sep. 29, 2022

Related U.S. Application Data

(60) Provisional application No. 62/870,653, filed on Jul. 3, 2019.

(51) Int. Cl.
| | | |
|---|---|---|
| C07C 21/18 | (2006.01) | |
| C07C 17/04 | (2006.01) | |
| C07C 17/20 | (2006.01) | |
| C07C 17/389 | (2006.01) | |
| C07C 17/23 | (2006.01) | |

(52) U.S. Cl.
CPC .......... C07C 17/04 (2013.01); C07C 17/204 (2013.01); C07C 17/389 (2013.01); C07C 21/18 (2013.01); C07C 17/23 (2013.01)

(58) Field of Classification Search
CPC ...................................................... C07C 21/18
See application file for complete search history.

(56) References Cited

U.S. PATENT DOCUMENTS

| | | | |
|---|---|---|---|
| 2014/0275649 A1 | 9/2014 | Wang et al. | |
| 2016/0355453 A1* | 12/2016 | Ohkubo | B01J 23/466 |
| 2017/0327441 A1 | 11/2017 | Lv et al. | |
| 2018/0134639 A1* | 5/2018 | Takeuchi | B01J 23/44 |

FOREIGN PATENT DOCUMENTS

| | | |
|---|---|---|
| CN | 103524293 A | 1/2014 |
| CN | 103508840 B | 5/2015 |
| CN | 105377797 A | 3/2016 |
| CN | 105753636 A | 7/2016 |
| CN | 105753638 B | 8/2018 |
| EP | 3020695 A1 | 5/2016 |
| WO | 2012061022 A2 | 5/2012 |
| WO | 2012115930 | 8/2012 |
| WO | 201936049 A1 | 2/2019 |

OTHER PUBLICATIONS

Mao et al., Highly Selective Dehydrochlorination of 1,1,1,2-Tetrafluoro-2-chloropropane to 2,3,3,3-Tetrafluoropropene over Alkali Metal Fluoride Modified MgO Catalysts, 2017, pp. 824-832, vol. 9, ChemCatChem, Wiley-VCH Verlag GmbH & Co. KgaA, Weinheim.
PCT International Search Report and Written Opinion for International Application No. PCT/US2020/040403 mailed Jan. 13, 2021.
Office Action dated Feb. 20, 2024 in Japanese Application No. 2022-500088 (with English translation).

* cited by examiner

*Primary Examiner* — Medhanit W Bahta

(57) ABSTRACT

A method of synthesizing 2,3,3,3-tetrafluoropropene (1234yf) from 2-chloro-3,3,3-trifluoropropene (1233xf). The 2-chloro-3,3,3-trifluoropropene (1233xf) is reacted in the vapor phase, in the presence of a catalyst, at a temperature and pressure sufficient to selectively convert the 2-chloro-3,3,3-trifluoropropene (1233xf) to 2,3,3,3-tetrafluoropropene (1234yf) without the use of antimony-based catalysts.

10 Claims, No Drawings

COMPOSITIONS AND METHODS FOR SYNTHESIS OF 2,3-DICHLORO-1,1,1,2-TETRAFLUORO-PROPANE AND 2,3,3,3-TETRAFLUOROPROPENE

This application claims the benefit of Application No. 62/870,653 filed on Jul. 3, 2019. The disclosure of Application No. 62/870,653 is hereby incorporated by reference.

FIELD

The present invention is directed to a method of synthesis of hydrofluoro-olefins (HFOs). More particularly, the present invention is directed to compositions and methods for the synthesis of 2,3-Dichloro-1,1,1,2-tetrafluoropropane and 2,3,3,3-tetrafluoropropene.

BACKGROUND

Hydrofluorocarbons (HFCs), such as hydrofluoro-olefins, have been disclosed as effective refrigerants, fire extinguishants, heat transfer media, propellants, foaming agents, blowing agents, gaseous dielectrics, sterilant carriers, polymerization media, particulate removal fluids, carrier fluids, buffing abrasive agents, displacement drying agents and power cycle working fluids. Hydrofluoro-olefins have replaced chlorofluorocarbons and hydrochlorofluorocarbons, which can potentially damage the Earth's ozone layer. Hydrofluoro-olefins do not contain chlorine, and, thus cannot degrade the Earth's ozone layer. Hydrofluoro-olefins additionally have low global warming potentials compared to hydrofluorocarbons, which reduces their $CO_2$ equivalent footprint.

2,3,3,3-tetrafluoropropene, (1234yf), is an environmentally friendly hydrofluoro-olefin used as a replacement for various chlorofluorocarbons and hydrochlorofluorocarbons. Conventional production of 2,3,3,3-tetrafluoro-2-propene, (1234yf), generally focuses on two synthesis pathways.

The first conventional pathway contains a step which strong lewis catalysts such as antimony-based catalysts (e.g., Sb+5) during the conversion of 2-chloro-3,3,3-trifluoropropene (1233xf) to 2-chloro-1,1,1,2 tetrafluoropropane (244bb), then convert 244bb to 2,3,3,3-tetrafluoropropene, (1234yf). Antimony halide catalysts and their combination with HF are highly corrosive to the process equipment resulting in processes which are difficult to operate. Antimony halide catalysts are additionally expensive to procure.

The second conventional pathway for the conversion of 2-chloro-3,3,3-trifluoropropene (1233xf) to 2,3,3,3-tetrafluoro-2-propene, (1234yf), proceeds via vapor phase hydrofluorination with a catalyst. The process exhibits poor yield and poor selectivity. Numerous undesired by-products are formed requiring extensive purification of the 2,3,3,3-tetrafluoropropene, (1234yf), prior to use.

A synthesis method for 2,3,3,3-tetrafluoropropene, (1234yf), which improves the yield and selectivity resulting in lower costs and ease of manufacture, in comparison to the conventional synthesis routes, would be desirable in the art.

1-chloro-2,3,3,3-tetrafluoropropene (1224yd) was also developed as new low GWP nonflammable refrigerant. One conventional process for the synthesis of 1224yd involves chlorinating 1234yf to 2,3-dichloro-1,1,1,2-tetrafluoro-propane (234bb), then dehydrochlorinating 234bb to 1224yd. A synthesis method for 1224yd, with lower costs and ease of manufacture, in comparison to the conventional synthesis routes, would be also desirable in the art.

SUMMARY

In one embodiment, disclosed herein is a method of synthesizing 2,3,3,3-tetrafluoropropene (1234yf). The method comprises contacting 2-chloro-3,3,3-trifluoropropene (1233xf) in the vapor phase or liquid phase with chlorine gas in the presence of a first catalyst to form 1,2,2-trichloro-3,3,3-trifluoro-propane (233ab); recovering the 233ab; contacting the 233ab in the vapor phase or liquid phase with hydrogen fluoride to form 2,3-dichloro-1,1,1,2-tetrafluoro-propane (234bb); contacting the 234bb in the vapor phase with hydrogen gas in the presence of a second catalyst to form 1234yf.

According to any combination of the foregoing embodiments, also disclosed herein are methods wherein the first catalyst is at least one of Lewis Acid, Lewis acid loaded on carbon and activated carbon.

According to any combination of the foregoing embodiments, also disclosed herein are methods wherein the first catalyst includes at least one of Ferric Chloride ($FeCl_3$) and activated carbon.

According to any combination of the foregoing embodiments, also disclosed herein are methods wherein the second catalyst includes copper on carbon (Cu/C) or gold on aluminum oxide ($Au/Al_2O_3$).

According to any combination of the foregoing embodiments, also disclosed herein are methods wherein the 233ab is contacted with the hydrogen fluoride with or without the presence of a third catalyst.

According to any combination of the foregoing embodiments, also disclosed herein are methods, wherein the third catalyst is a fluorination catalyst selected from the group consisting of activated carbon, alumina, chromium oxide, oxides of transition metals, metal halides and combinations thereof.

According to any combination of the foregoing embodiments, also disclosed herein are methods wherein the reaction is essentially free of antimony pentahalides.

In another embodiment, disclosed herein is a method of synthesizing 1234yf comprising: contacting 1233xf in the vapor phase or liquid phase with chlorine gas and hydrogen fluoride with or without the presence of a first catalyst to form 234bb; contacting 234bb in the vapor phase with hydrogen gas the presence of a second catalyst to form 1234yf.

According to any combination of the foregoing embodiments, also disclosed herein are methods wherein the first catalyst is a Lewis Acid.

According to any combination of the foregoing embodiments, also disclosed herein are methods wherein the first catalyst includes Ferric Chloride ($FeCl_3$).

According to any combination of the foregoing embodiments, also disclosed herein are methods wherein the second catalyst includes copper on carbon (Cu/C) or gold on aluminum oxide ($Au/Al_2O_3$).

According to any combination of the foregoing embodiments, also disclosed herein are methods wherein the reaction is essentially free of antimony pentahalide.

According to any combination of the foregoing embodiments, also disclosed herein are compositions comprising 2,3,3,3-tetrafluoropropene formed by the above methods.

In another embodiment, disclosed herein is a method of synthesizing 1-chloro-2,3,3,3-tetrafluoropropene comprising:

contacting 2-chloro-3,3,3-trifluoropropene in the vapor phase or liquid phase with chlorine gas in the presence of a first catalyst to form 1,2,2-trichloro-3,3,3-trifluoropropane;

recovering the 1,2,2-trichloro-3,3,3-trifluoro-propane;

contacting the 1,2,2-trichloro-3,3,3-trifluoro-propane in the vapor phase or liquid phase with hydrogen fluoride to form 2,3-dichloro-1,1,1,2-tetrafluoro-propane;

dehydrochlorinate 2,3-dichloro-1,1,1,2-tetrafluoro-propane to 1-chloro-2,3,3,3-tetrafluoropropene in liquid phase with a caustic or in the vapor phase with or without a catalyst.

In another embodiment, disclosed herein is a method of synthesizing 1-chloro-2,3,3,3-tetrafluoropropene comprising:

contacting 2-chloro-3,3,3-trifluoropropene with chlorine gas and hydrogen fluoride optionally in the presence of a first catalyst to form 2,3-dichloro-1,1,1,2-tetrafluoropropane;

dehydrochlorinating 2,3-dichloro-1,1,1,2-tetrafluoro-propane to form 1-chloro-2,3,3,3-tetrafluoropropene.

According to any combination of the foregoing embodiments, also disclosed herein are methods wherein 2,3-dichloro-1,1,1,2-tetrafluoro-propane is dehydrochlorinated to form 1-chloro-2,3,3,3-tetrafluoropropene in a liquid phase with at least one caustic.

In another embodiment, disclosed herein is a composition comprising 234bb and 234da and at least one additional compound selected from the group consisting of 1234yf, 1243zf, 1233xf, 245cb, CF3COF, CHCl3, 234bb(Br), 243ab, 1224yd, 224bb, 243db, 243dbB, C6H3Cl2F7, and CF3CFClCH2OCH2CFClCF3.

In another embodiment, disclosed herein is a composition comprising 1224yd and 1233xf and at least one additional compound selected from the group consisting of 1234yf, 1243zf, 245cb, 244bb, 1233xf(Br), 243db, 1223xd, 1-chloro-trifluoropropyne, 3,3,3-trifluoropropyne, 1215yb, 1224xe, 253fb, 1214ya, 123, and 124.

The various aspects and embodiments of the disclosure can be used alone or in combinations with each other. Other features and advantages of the present invention will be apparent from the following more detailed description, which illustrate, by way of example, the principles of the invention.

DETAILED DESCRIPTION

The foregoing general description and the following detailed description are exemplary and explanatory only and are not restrictive of the invention.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

The transitional phrase "consisting of" excludes any element, step, or ingredient not specified. If in the claim such would close the claim to the inclusion of materials other than those recited except for impurities ordinarily associated therewith. When the phrase "consists of" appears in a clause of the body of a claim, rather than immediately following the preamble, it limits only the element set forth in that clause; other elements are not excluded from the claim as a whole.

The transitional phrase "consisting essentially of" is used to define a composition, method that includes materials, steps, features, components, or elements, in addition to those literally disclosed provided that these additional included materials, steps, features, components, or elements do materially affect the basic and novel characteristic(s) of the claimed invention, especially the mode of action to achieve the desired result of any of the processes of the present invention. The term 'consisting essentially of' occupies a middle ground between "comprising" and 'consisting of'.

Where applicants have defined an invention or a portion thereof with an open-ended term such as "comprising," it should be readily understood that (unless otherwise stated) the description should be interpreted to also include such an invention using the terms "consisting essentially of" or "consisting of."

Also, use of "a" or "an" are employed to describe elements and components described herein. This is done merely for convenience and to give a general sense of the scope of the invention. This description should be read to include one or at least one and the singular also includes the plural unless it is obvious that it is meant.

The term "selectivity," as used herein, means the ratio of the numbers of moles of the desired product to the number of moles of undesired products expressed as a percentage.

The term "yield," as used herein, means the ratio of the amount of product produced to the theoretical maximum amount of product, based on the amount of the limiting reagent.

Unless otherwise defined, all technical and scientific terms used herein have the same meaning as commonly understood by one of ordinary skill in the art to which this invention belongs. In case of conflict, the present specification, including definitions, will control. Although methods and materials similar or equivalent to those described herein can be used in the practice or testing of embodiments of the present invention, suitable methods and materials are described below. In addition, the materials, methods, and examples are illustrative only and not intended to be limiting.

Provided is a method of making hydrofluoro-olefins (HFOs) from hydrochloro-olefin and hydrochlorofluoro-olefin reagents and intermediates. In an exemplary embodiment, 2,3,3,3-tetrafluoropropene (1234yf) is produced, via a multi-step process, from 2-chloro-3,3,3-trifluoropropene (1233xf). In some embodiments, the method is free or essentially free of antimony pentahalides. By "essentially free" it is meant that the reagents, intermediates and products contain less than 100 ppm antimony (V) containing compounds.

The process may be conducted in any reactor suitable for a vapor phase or liquid phase fluorination reaction. The reactor is made of a material that is resistant to the reactants employed. The reactor may be constructed from materials which are resistant to the corrosive effects of hydrogen fluoride such as stainless steel, Hastelloy, Inconel, Monel, gold or gold-lined or quartz. The reactions may be conducted batchwise, continuous, semi-continuous or combinations thereof. Suitable reactors include batch reactor vessels and tubular reactors.

In an embodiment, 2-chloro-3,3,3-trifluoropropene (1233xf) is charged to a reactor, heated, and contacted in the presence of a catalyst, with chlorine $Cl_2$ at a temperature and pressure sufficient to effect chlorination to form 2,2,3-trichloro-1,1,1-trifluoropropane (233ab), as shown in Scheme (1).

Suitable catalysts include Lewis acids. In one embodiment, the catalyst is at least one of ferric chloride (FeCl$_3$) or activated carbon. In some embodiments, the reaction mixture is heated to a temperature in the range of 50° C. to 175° C. In some embodiments, the reaction is performed at a reactor pressure of 1 pound per square inch gauge (psig) to 300 pounds per square inch gauge (psig). In another embodiment, the reaction is performed with agitation. In a further embodiment, the reaction is performed with an optional he catalyst. When employed, the catalyst is present in an amount of less than 2% of total weight of reaction mixture, greater than 0% and less than about 2% and, in some cases, about 0.1% to about 1.5%. The selectivity to 233ab is from about 60% to about 99.9%, about 65% to about 99% and, in some cases about 80 to about 95%. The yield of reaction is from about 60% to about 99.9%, about 80% to about 99% and, in some cases, about 90 to about 98%%. The molar ratio of Cl$_2$/1233xf can range from about 2 to about 0.1. In a further embodiment, the reaction is performed by using UV light at atmosphere pressure, subatmospheric pressure or vacuum at temperature from about 0° C. to about 150° C.

The 2,2,3-trichloro-1,1,1-trifluoropropane (233ab) may be recovered from the reaction and charged to a second reactor. The 2,2,3-trichloro-1,1,1-trifluoropropane (233ab) is then heated, and contacted, in the vapor phase or liquid phase with hydrogen fluoride (HF) at a temperature and pressure sufficient to effect fluorination to form 2,3-dichloro-1,1,1,2-tetrafluoro-propane (234bb), as shown in Scheme (2). In some embodiments, the reaction mixture is heated to a temperature of 50° C. to 175° C. In some embodiments, the reaction is performed at a reactor pressure of 1 psig to 300 psig. In some embodiments, the reaction of Scheme (2) may be performed without a catalyst. In some embodiments, the reaction of Scheme (2) may be performed in the presence of a catalyst. In one embodiment, the catalyst includes a Lewis Acid. In one embodiment, the reaction is performed while being agitated. Catalyst can range from 0 to 20%, greater than 0 to about 15% and, in some cases, about 5 to about 10% by weight of total reactants. The molar ratio of HF/233ab can range from about 0.2 to about 30, about 0.5 to about 25 and, in some cases, about 1 to about 10. The selectivity to 234bb can range from about 50% to about 99%, about 70 to 95% and, in some cases, about 75 to about 90%.

The 2,3-dichloro-1,1,1,2-tetrafluoro-propane (234bb) is then heated, and contacted, in the vapor phase with hydrogen (H$_2$), in the presence of a catalyst, at a temperature and pressure sufficient to effect hydrogenation to form 1,1,1,2-tetrafluoro-2-propene (1234yf), as shown in Scheme (3). In one embodiment, the reaction temperature ranges from about 180 C to about 400 C, about 200 to about 350 and, in some cases, about 225 to about 325 C. The catalyst can comprise at least one of Cu/C and or Au/Al$_2$O$_3$. The catalyst contact time can range from about 10 second to about 120 seconds, about 25 to about 100 seconds and, in some cases, about 50 to about 75 seconds. Selectivity to 1234yf can range from about 80% to about 99%, about 85 to about 98 and, in some cases, about 90 to 95%.

Suitable catalysts include copper on carbon (Cu/C) and gold on aluminum oxide (Au/Al$_2$O$_3$). In some embodiments, the reaction mixture is heated to a temperature of 50° C. to 300° C. In some embodiments, the reaction is performed at a reactor pressure of 1 psig to 300 psig.

In an alternate embodiment, the synthesis steps of Scheme (1) and Scheme (2) above may be combined into a single process step. The 2-chloro-3,3,3-trifluoropropene (1233xf) is charged to a reactor, heated, and contacted, in the vapor phase or liquid phase, with or without the presence of a catalyst, with chlorine gas (Cl$_2$) and hydrogen fluoride (HF), at a temperature and pressure sufficient to effect conversion to 2,3-dichloro-1,1,1,2-tetrafluoro-propane (234bb), as shown in Scheme (4).

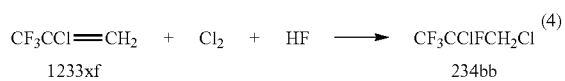

The catalysts and reaction conditions for Scheme (4) are the same as discussed above for Schemes (1) and (2). The resulting 2,3-dichloro-1,1,1,2-tetrafluoro-propane (234bb) may be converted to 2,3,3,3-tetrafluoropropene, (1234yf) via Scheme (3) as discussed above.

In a further embodiment, 234bb may be converted to 1-chloro-2,3,3,3-tetrafluoropropene by reacting with aqueous caustic with or without present of a catalyst at a temperature sufficient to convert 234bb to 1224yd, as shown in Scheme (5) below. For example, the reaction can be conducted at a temperature from about 20 C to about 100 C, about 25 to about 80 C and, in some cases, about 30 to 75 C and with or without a phase transfer catalyst. When employed the phase transfer catalyst can comprise about 0.1% to about 3%, about 0.25% to about 2.5% and, in some cases, about 0.5 to about 2% by weight of total reactant. The mol ratio of Caustic/234bb and range from about 0.1 to about 2, about 0.25 to about 1.75 and, in some cases, about 0.5 to about 1.5. The selectivity to 1224yd is range from 80% to 99%, about 85% to 99% and, in some cases, about 90 to 99%.

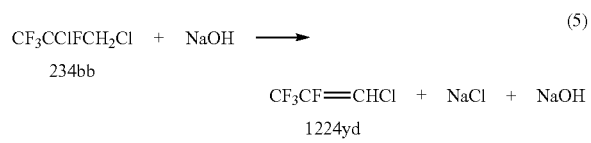

The reactions may be conducted batch wise, continuous, semi-continuous or combinations thereof. Aqueous caustic can be a strong base, such as at least one of sodium hydroxide, potassium hydroxide, potassium tert-butoxide, calcium oxides, or calcium hydroxide. The molar ratio of base to 234bb can range from about 0.1 to about 2, about 0.5 to about 1.75 and, in some cases, about 0.75 to about 1.5. Desirable results have been obtained from using a base comprising NaOH or KOH. The liquid phase dehydrochlorination may be performed in the presence or absence of a phase transfer catalyst. In some embodiments, the phase transfer catalyst may include a quaternary ammonium salt, a phosphonium salt, or a crown ether. The amount of phase transfer catalyst can range from about 0.5 to about 3% by weight, about 1 to about 2.5% and, in some cases, about 1.5 to about 2%. Desirable results can be obtained by using quaternary ammonium.

In a further embodiment, 234bb from Reaction Scheme (2) or (4) can be employed in Reaction Scheme (5) and, in a particular aspect, Reaction Schemes (2) or (4) and (5) are integrated.

In another embodiment, 234bb may be converted to 1224yd through a vapor phase dehydrochlorination with or without present of a catalyst as shown in Scheme (6) below.

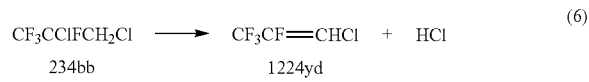

(6)

In the temperature range of about 200° C. to about 550 C, about 250 to about 500° C. and, in some cases, about 300 to about 450° C. and with contact time from 10 to 120 seconds, about 20 to about 100 seconds and, in some cases, about 25 to 75 seconds and with selectivity from about 90% to about 99% and, in some cases, about 95 to about 99%.

In a further embodiment, 234bb from Reaction Scheme (2) or (4) can be employed in Reaction Scheme (6) and, in a particular aspect, Reaction Schemes (2) or (4) and (6) are integrated.

In one embodiment, the dehydrochlorination of Scheme (6) is a thermally driven process in the presence of a dehydrochlorination catalyst. Suitable catalysts include at least one of activated carbon, alumina, chromium oxide, oxides of transition metals, metal halides, and combinations thereof. Desirable results can be obtained by using activated and metal halide on carbon catalysts such as KCl on carbon. In the temperature range of 200 C to 550 C, about 250 to about 500 C and, in some cases, about 275 to 450 C and with contact time from about 10 seconds to 120 seconds, about 20 to about 100 and, in some cases, about 25 to about 75 seconds and with selectivity from 90% to 99% and about 95 to 99%.

In one embodiment, disclosed herein is a composition comprising 2,3,3,3 tetrafluoropropene and at least one additional compound selected from the group consisting of 254eb, 263fb and 234bb. These compositions can be produced by a process described herein or obtained by blending components of the composition. The amount of this additional compound can range from greater than 0 to about 1%, about 0 to about 0.5% and, in some cases, about 0 to about 0.1%, and the remainder comprising 1234yf.

In one embodiment, disclosed herein is a composition comprising 2,3,3,3-tetrafluoropropene and at least one additional compound selected from the group consisting of 244bb, 244eb, 1233xf, and 263fb. These compositions can be produced by a process described herein or obtained by blending components of the composition. The amount of this additional compound can range from greater than 0 to about 1%, about 0 to about 0.5% and, in some cases, about 0 to about 0.1%, and the remainder comprising 1234yf.

In another embodiment, disclosed herein is a composition comprising 234bb, 234da and at least one additional compound selected from the group consisting of 1234yf, 1243zf, CF3COF, CHCl3, 234bb(Br), 1224yd, 224bb, 243db, 243db (B), 243ab, C6H3Cl2F7, and CF3CFClCH2OCH2CFClCF3. These compositions can be produced by a process described herein or obtained by blending components of the composition. The amount of this additional compound can range from greater than 0 to about 10%, greater than about 0 to about 5%, and in some cases, greater than about 0 to about 1% and the remainder comprising 234bb and 234da.

In another embodiment, disclosed herein is a composition comprising 1224yd, 1233xf and at least one additional compound selected from the group consisting of 1234yf, 1243zf, 244bb, 1233xf(Br), 243db, 1223xd, 1-chloro-trifluoropropyne, 3,3,3-trifluoropropyne, 1215yb, 1224xe, 253fb, 1214ya, 123, and 124. The amount of this additional compound can range from greater than 0 ppm to 10 wt %; about 5 ppm to about 8% and in some cases, about 20 ppm to about 1%. The amount of 1224yd and 1233xf can range, respectively, from 90% to 99.99%. These compositions can be produced by a process described herein or obtained by blending components of the composition.

The following Examples are provided to illustrate certain aspects and embodiments of the invention and shall not limit the scope of the appended claims.

EXAMPLES

Example 1: 1233xf Chlorination to 233ab 0.9 g Anhydrous FeCl3 was loaded into a 400 ml Hastelloy C shaker tube. Then the autoclave was evacuated. Then 196 g 1233xf and 107 g Cl2 were added into the reactor. The mixture was heated to 85° C. and agitated at 85° C. for 2.5 hours. After the reactor was cooled down to room temperature, the product was analyzed by GC-MS-FID using a capillary GC column without packing. The GC analysis of the product is listed in Table 1.

TABLE 1

| Compounds | | GC-FID area % |
|---|---|---|
| 245cb | CF3CF2CH3 | 0.0333% |
| 254eb | CF3CFHCH3 | 0.0160% |
| 244bb | CF3CFClCH3 | 0.8682% |
| 1233xf | CF3CCl=CH2 | 0.3807% |
| Z-1223xd | CF3CCl=CHCl | 0.1697% |
| E-1223xd | CF3CCl=CHCl | 0.6793% |
| 233ab | CF3CCl2CH2Cl | 97.4649% |
| 233da | CF3CHClCHCl2 | 0.0075% |
| 1231xf | CFCl2CCl=CH2 | 0.0057% |
| 1223 isomer | | 0.0145% |
| 223db | CF3CHClCCl3 | 0.1353% |
| C2HCl5 | | 0.0161% |
| C4HCl3F4 | | 0.0162% |
| Others | | 0.1926% |

Example 2: 1233xf Chlorofluorination to 234bb 433 g HF, 68.25 ml 1233xf and 45 g Cl2 were added into a one-liter autoclave. It was heated to 90° C. and stayed at 90° C. for 220 minutes with agitation. After the reactor was cooled down to room temperature, the product was quenched into ice and dichlorobenzene and washed by KOH solution. Then the product was analyzed by GC-MS-FID using a capillary GC column without packing. The GC analysis of the product is listed in Table 2. The product concentration in the table was normalized without dichlorobenzene.

TABLE 2

| Compounds | | GC area % |
|---|---|---|
| Z-1224yd | Z-CF3CF=CHCl | 0.1900% |
| 1233xf | CF3CCl=CH2 | 8.5851% |
| E-1224yd | E-CF3CF=CHCl | 0.0899% |
| Z-1223xd | Z-CF3CCl=CHCl | 2.8589% |
| 234bb | CF3CFClCH2Cl | 77.2767% |
| 243ab | CF3CCl2CH3 | 8.9155% |
| 234da | CF3CHClCHClF | 0.3194% |
| E-1223xd | E-CF3CCl=CHCl | 0.3486% |
| 234da | CF3CHClCHClF | 0.8006% |
| 233ab | CF3CCl2CH2Cl | 0.2068% |
| 233da | CF3CHClCHCl2 | 0.0367% |
| others | | 0.3717% |

Example 3: Hydrodechlorination of 234bb to 1234yf

Example 3 demonstrates the conversion of 234bb into 1234yf over 10 wt % Cu/C catalyst. 10 cc 10 wt % Cu on acid washed carbon catalyst granules were loaded into a ½ inch Hastelloy C reactor. The catalyst was conditioned at about 250° C. with 50 ccm/min $H_2$ for 2 hours. The hydrodechlorination of 234bb was studied at a temperature range of about 200° C.-300° C. and the products indicated in Table 4. Products of the reaction were analyzed by GC-MS using a capillary GC column without packing to give the GC-MS area % as listed in Table 3.

TABLE 3

| Temp | H₂/234bb | Contact Time, | GC-MS area % | |
|---|---|---|---|---|
| ° C. | mole ratio | sec | 1234yf | 234bb |
| 200 | 1.2:1 | 30 | 5.55% | 94.05% |
| 199 | 1.2:1 | 30 | 2.71% | 97.13% |
| 250 | 1.2:1 | 30 | 11.17% | 88.47% |
| 249 | 1.2:1 | 30 | 7.64% | 92.03% |
| 299 | 1.2:1 | 30 | 45.56% | 52.92% |
| 300 | 1.2:1 | 30 | 41.76% | 56.63% |

Example 4: Hydrodechlorination of 234bb to 1234yf

Example 4 demonstrates the conversion of 234bb into 1234yf over 5 wt % Ru/C catalyst. 10 cc 10 wt % Ru on acid washed carbon catalyst granules was loaded into a ½-inch Hastelloy C reactor. The catalyst was conditioned at 250° C. with 50 ccm/min $H_2$ for 2 hours. The hydrodechlorination of 234bb was studied at a temperature range of 100° C.-200° C. and the products indicated in Table 4. Products of the reaction were analyzed by GC-MS using a capillary GC column without packing to give the GC-MS area % as listed in Table 4.

TABLE 4

| Temp | H₂/234bb | Contact Time, | GC-MS area % | | | |
|---|---|---|---|---|---|---|
| ° C. | mole ratio | sec | 1234yf | 254eb | 263fb | 234bb |
| 98 | 1.2:1 | 30 | 1.41% | 1.61% | 0.18% | 95.04% |
| 99 | 1.2:1 | 30 | 1.76% | 1.28% | 0.15% | 96.82% |
| 123 | 1.2:1 | 30 | 5.40% | 2.22% | 0.36% | 92.03% |
| 124 | 1.2:1 | 30 | 5.12% | 18.86% | 2.27% | 73.75% |
| 156 | 1.2:1 | 30 | 25.86% | 4.58% | 1.09% | 68.26% |
| 152 | 1.2:1 | 30 | 25.39% | 4.10% | 0.95% | 69.37% |
| 172 | 1.2:1 | 30 | 69.41% | 6.22% | 1.91% | 21.86% |
| 173 | 1.2:1 | 30 | 67.35% | 4.65% | 1.40% | 26.05% |
| 200 | 1.2:1 | 30 | 73.17% | 13.81% | 11.05% | 0.00% |
| 202 | 1.2:1 | 30 | 82.55% | 9.34% | 5.98% | 0.00% |

Example 5: Chlorination of 1234yf to 234bb 180 g 1234yf was mixed with 112 g Cl2 and 1 g anhydrous FeCl3 as catalyst. The reactor was heated to 80° C. with agitation and the agitated at 80° C. for 4 hours. The liquid phase of product was rotavapored to remove FeCl3 and then was analyzed by GC-MS-FID using a capillary GC column without packing as listed in Table 5.

TABLE 5

| Compounds | Structure | GC FID area % |
|---|---|---|
| | CF3COF | 0.0023% |
| 1234yf | CF3CF=CH2 | 0.1122% |
| | CF3CH2CClO | 0.0033% |
| 30 | CH2Cl2 | 0.0445% |
| 234bb | CF3CFClCH2Cl | 99.7054% |
| 20 | CHCl3 | 0.0020% |
| Unknown | Unknown | 0.0017% |
| 234bbBr | CF3CFBrCH2Cl (234bbBr) | 0.0012% |
| 234da | CF3CHClCHClF | 0.0167% |
| 224bb | CF3CFClCHCl2 | 0.0713% |
| Unknown | Unknown | 0.0013% |
| C6H3Cl2F7 | C6H3Cl2F7 | 0.0092% |
| C6H3Cl2F7 | C6H3Cl2F7 | 0.0095% |
| CF3CFClCH2OCH2CFClCF3 | CF3CFClCH2OCH2CFClCF3 | 0.0135% |
| CF3CFClCH2OCH2CFClCF3 | CF3CFClCH2OCH2CFClCF3 | 0.0029% |

Example 6: Chlorination of 1234yf to 234bb 180 g 1234yf was mixed with 112 g $Cl_2$ and 1 g anhydrous FeCl3 as catalyst and heated to 100° C. with agitation and then agitated at 100° C. for 6 hours with. The liquid phase of product was rotavapored to remove FeCl3 and then was analyzed by GC-MS-FID using a capillary GC column without packing as listed in Table 6.

TABLE 6

| | Compounds | GC-FID area % |
|---|---|---|
| HFP | CF3CF=CF2 | 0.0007% |
| 1234yf/1225ye | CF3CF=CH2/CF3CF=CHF | 0.6896% |
| 1224yd-Z | Z-CF3CF=CHCl | 0.0132% |
| 1224yd-E | E-CF3CF=CHCl | 0.0057% |
| 160 | CH3CH2Cl | 0.0027% |
| 225ca | CF3CF2CHCl2 | 0.0253% |
| 225cb | CClF2CF2CHClF | 0.0149% |
| 234bb | CF3CClFCH2Cl | 99.0218% |
| 234da | CF3CHClCHClF | 0.0018% |
| 234da | CF3CHClCHClF | 0.0028% |
| 243db | CF3CHClCH2Cl | 0.1126% |

TABLE 6-continued

| Compounds | | GC-FID area % |
|---|---|---|
| 1232 | C3H2Cl2F2 | 0.0028% |
| 234 isomer | C3H2Cl2F4 | 0.0029% |
| 224ba | CClF2CClFCHClF | 0.0305% |
| 243db(B) | CF3CHBrCH2Cl | 0.0067% |
|  | C6H3Cl2F7 | 0.0210% |
|  | C6H3Cl2F7 | 0.0222% |
|  | CF3CFClCH2OCH2CFClCF3 | 0.0195% |
|  | CF3CFClCH2OCH2CFClCF3 | 0.0033% |

Example 7: Dehydrochlorination of 234bb to 1224yd 150 g 234bb was mixed with 200 g 32 wt % KOH and heated to 90° C. with agitation and then agitated at 90° C. for 6 hours. After reactor was cooled down to room temperature, the liquid phase of product was collected and analyzed by GC-MS-FID using a capillary GC column without packing as listed in Table 7.

TABLE 7

| Compounds | | GC FID area % |
|---|---|---|
| 23 | CHF3 | 0.0034% |
| 1234yf | CF3CF=CH2 | 0.0007% |
| 3,3,3-trifluoropropyne | CF3C≡CH | 0.0002% |
| 1243zf | CF3CH=CH2 | 0.0018% |
| 245eb | CF3CHFCHF2 | 0.0003% |
| 1-chloro-trifluoropropyne | CF3C≡CCl | 0.0821% |
| 1224yd-Z | Z-CF3CF=CHCl | 84.9299% |
| 1233xf | CF3CCl=CH2 | 0.1436% |
| 1224yd-E | E-CF3CF=CHCl | 4.8567% |
| 1223xd-Z | Z-CF3CCl=CHCl | 1.7065% |
| 234bb | CF3CClFCH2Cl | 7.0353% |
| 1223xd-E | E-CF3CCl=CHCl | 1.2123% |
| 243db | CF3CHClCH2Cl | 0.0272% |

Example 8: Dehydrochlorination of 234bb to 1224yd 150 g 234bb was mixed with 152 g 25 wt % NaOH and 1.5 g TBAB, it was heated to 40° C. with agitation and then agitated at 40° C. for 4 hours. The liquid phase of product was analyzed by GC-MS-FID using a capillary GC column without packing as listed in Table 8.

TABLE 8

| Compounds | | GC FID area % |
|---|---|---|
| 23 | CHF3 | 0.0047% |
| trifluoropropyne/1234yf | CF3C≡CH/CF3CF=CH2 | 0.0021% |
| 1243zf | CF3CH=CH2 | 0.0016% |
| 254eb | CF3CHFCH3 | 0.0013% |
| 124 | CF3CFHCl | 0.0007% |
| 245eb | CF3CHFCH2F | 0.0010% |
| 1215yb | CF3CF=CClF | 0.0521% |
| 1-chloro-3,3,3-trifluoropropyne | CF3C≡CCl | 0.2309% |
| 244bb | CF3CClFCH3 | 0.0044% |
| 1224yd-Z | Z-CF3CF=CHCl | 93.6878% |
| 1224xe-Z | Z-CF3CCl=CHF | 0.0049% |
| 1233xf | CF3CCl=CH2 | 0.0649% |
| 1224yd-E | E-CF3CF=CHCl | 4.3788% |
| 1224xe-E | E-CF3CCl=CHF | 0.0012% |
| 244 isomer | C3H3ClF4 | 0.0007% |
| 123 | CF3CHCl2 | 0.0011% |
| 253fb | CF3CH2CH2Cl | 0.0167% |
| 1233xfB | CF3CBr=CH2 | 0.0011% |
| 1214ya | CF3CF=CCl2 | 0.0018% |
| 1223xd-Z | 1223xd-Z | 0.0672% |
| 1223 isomer | C3HCl2F3 | 0.0050% |
| 234bb | CF3CClFCH2Cl | 1.4566% |
| 1223xd-E | E-CF3CCl=CHCl | 0.0120% |
| 243db | CF3CHClCH2Cl | 0.0006% |
| 112 | CFCl2CFCl2 | 0.0007% |

The following Examples 9 through 12 were generated using ThermPy software and illustrate the performance of certain inventive compositions under mobile conditions including cooling (COP_c and CAP_c) and heating (COP_h and CAP_h):

T_condenser=40.0° C.
T_evaporator=0.0° C.
superheat=15.0 K
compressor efficiency=0.7

Example 9: 98 wt % of R-1224yd and Additional Compounds R-1233xf and R-1234yf Table 9 illustrates that all blends of this Example have greater capacities and smaller COPs than R-1224yd. When the amount of Additional Compound ranges from pure R-1233xf to pure R-1234yf, CAP decreases and COP increases as the R-1233xf content increases from 0 to 2 wt-%. When the Additional Compound is R-1233xf (98% R-1224yd and 2% R-1233xf), the COP is the same as R-1224yd and the CAP is greater

TABLE 9

| Example 9 - fluid | T_discharge (° C.) | P_suction (MPa) | P_discharge (MPa) | compression ratio | evaporator glide (K) | condenser glide (K) |
|---|---|---|---|---|---|---|
| _R-1233xf_R-1234yf_R-1224yd_W=_0.0_0.02_0.98 | 65.99 | 0.0584 | 0.2592 | 4.438 | 0.916 | 1.966 |
| _R-1233xf_R-1234yf_R-1224yd_W=_0.0004_0.0196_0.98 | 65.97 | 0.0584 | 0.259 | 4.437 | 0.897 | 1.929 |
| _R-1233xf_R-1234yf_R-1224yd_W=_0.0008_0.0192_0.98 | 65.95 | 0.0583 | 0.2587 | 4.436 | 0.879 | 1.892 |
| _R-1233xf_R-1234yf_R-1224yd_W=_0.0012_0.0188_0.98 | 65.94 | 0.0583 | 0.2584 | 4.435 | 0.861 | 1.854 |
| _R-1233xf_R-1234yf_R-1224yd_W=_0.0016_0.0184_0.98 | 65.92 | 0.0582 | 0.2582 | 4.434 | 0.843 | 1.817 |
| _R-1233xf_R-1234yf_R-1224yd_W=_0.002_0.018_0.98 | 65.9 | 0.0582 | 0.2579 | 4.433 | 0.825 | 1.779 |
| _R-1233xf_R-1234yf_R-1224yd_W=_0.0024_0.0176_0.98 | 65.89 | 0.0581 | 0.2577 | 4.432 | 0.806 | 1.742 |

TABLE 9-continued

| | | | | | | |
|---|---|---|---|---|---|---|
| _R-1233xf_R-1234yf_R-1224yd_W=_0.0028_0.0172_0.98 | 65.87 | 0.0581 | 0.2574 | 4.431 | 0.788 | 1.704 |
| _R-1233xf_R-1234yf_R-1224yd_W=_0.0032_0.0168_0.98 | 65.85 | 0.058 | 0.2572 | 4.43 | 0.77 | 1.667 |
| _R-1233xf_R-1234yf_R-1224yd_W=_0.0036_0.0164_0.98 | 65.83 | 0.058 | 0.2569 | 4.429 | 0.752 | 1.629 |
| _R-1233xf_R-1234yf_R-1224yd_W=_0.004_0.016_0.98 | 65.82 | 0.058 | 0.2567 | 4.429 | 0.734 | 1.591 |
| _R-1233xf_R-1234yf_R-1224yd_W=_0.0044_0.0156_0.98 | 65.8 | 0.0579 | 0.2564 | 4.428 | 0.715 | 1.553 |
| _R-1233xf_R-1234yf_R-1224yd_W=_0.0048_0.0152_0.98 | 65.78 | 0.0579 | 0.2561 | 4.427 | 0.697 | 1.515 |
| _R-1233xf_R-1234yf_R-1224yd_W=_0.0052_0.0148_0.98 | 65.76 | 0.0578 | 0.2559 | 4.426 | 0.679 | 1.477 |
| _R-1233xf_R-1234yf_R-1224yd_W=_0.0056_0.0144_0.98 | 65.75 | 0.0578 | 0.2556 | 4.425 | 0.661 | 1.438 |
| _R-1233xf_R-1234yf_R-1224yd_W=_0.006_0.014_0.98 | 65.73 | 0.0577 | 0.2554 | 4.424 | 0.643 | 1.4 |
| _R-1233xf_R-1234yf_R-1224yd_W=_0.0064_0.0136_0.98 | 65.71 | 0.0577 | 0.2551 | 4.423 | 0.624 | 1.362 |
| _R-1233xf_R-1234yf_R-1224yd_W=_0.0068_0.0132_0.98 | 65.69 | 0.0576 | 0.2549 | 4.422 | 0.606 | 1.323 |
| _R-1233xf_R-1234yf_R-1224yd_W=_0.0072_0.0128_0.98 | 65.68 | 0.0576 | 0.2546 | 4.421 | 0.588 | 1.285 |
| _R-1233xf_R-1234yf_R-1224yd_W=_0.0076_0.0124_0.98 | 65.66 | 0.0575 | 0.2543 | 4.42 | 0.57 | 1.246 |
| _R-1233xf_R-1234yf_R-1224yd_W=_0.008_0.012_0.98 | 65.64 | 0.0575 | 0.2541 | 4.419 | 0.552 | 1.207 |
| _R-1233xf_R-1234yf_R-1224yd_W=_0.0084_0.0116_0.98 | 65.62 | 0.0575 | 0.2538 | 4.418 | 0.533 | 1.168 |
| _R-1233xf_R-1234yf_R-1224yd_W=_0.0088_0.0112_0.98 | 65.6 | 0.0574 | 0.2536 | 4.417 | 0.515 | 1.129 |
| _R-1233xf_R-1234yf_R-1224yd_W=_0.0092_0.0108_0.98 | 65.59 | 0.0574 | 0.2533 | 4.416 | 0.497 | 1.09 |
| _R-1233xf_R-1234yf_R-1224yd_W=_0.0096_0.0104_0.98 | 65.57 | 0.0573 | 0.2531 | 4.415 | 0.479 | 1.051 |
| _R-1233xf_R-1234yf_R-1224yd_W=_0.01_0.01_0.98 | 65.55 | 0.0573 | 0.2528 | 4.414 | 0.461 | 1.012 |
| _R-1233xf_R-1234yf_R-1224yd_W=_0.0104_0.0096_0.98 | 65.53 | 0.0572 | 0.2525 | 4.413 | 0.442 | 0.973 |
| _R-1233xf_R-1234yf_R-1224yd_W=_0.0108_0.0092_0.98 | 65.51 | 0.0572 | 0.2523 | 4.412 | 0.424 | 0.933 |
| _R-1233xf_R-1234yf_R-1224yd_W=_0.0112_0.0088_0.98 | 65.5 | 0.0571 | 0.252 | 4.411 | 0.406 | 0.894 |
| _R-1233xf_R-1234yf_R-1224yd_W=_0.0116_0.0084_0.98 | 65.48 | 0.0571 | 0.2518 | 4.41 | 0.388 | 0.854 |
| _R-1233xf_R-1234yf_R-1224yd_W=_0.012_0.008_0.98 | 65.46 | 0.057 | 0.2515 | 4.409 | 0.37 | 0.815 |
| _R-1233xf_R-1234yf_R-1224yd_W=_0.0124_0.0076_0.98 | 65.44 | 0.057 | 0.2513 | 4.408 | 0.352 | 0.775 |
| _R-1233xf_R-1234yf_R-1224yd_W=_0.0128_0.0072_0.98 | 65.42 | 0.057 | 0.251 | 4.406 | 0.333 | 0.735 |
| _R-1233xf_R-1234yf_R-1224yd_W=_0.0132_0.0068_0.98 | 65.4 | 0.0569 | 0.2507 | 4.405 | 0.315 | 0.695 |
| _R-1233xf_R-1234yf_R-1224yd_W=_0.0136_0.0064_0.98 | 65.39 | 0.0569 | 0.2505 | 4.404 | 0.297 | 0.655 |
| _R-1233xf_R-1234yf_R-1224yd_W=_0.014_0.006_0.98 | 65.37 | 0.0568 | 0.2502 | 4.403 | 0.279 | 0.615 |
| _R-1233xf_R-1234yf_R-1224yd_W=_0.0144_0.0056_0.98 | 65.35 | 0.0568 | 0.25 | 4.402 | 0.261 | 0.575 |
| _R-1233xf_R-1234yf_R-1224yd_W=_0.0148_0.0052_0.98 | 65.33 | 0.0567 | 0.2497 | 4.401 | 0.243 | 0.534 |
| _R-1233xf_R-1234yf_R-1224yd_W=_0.0152_0.0048_0.98 | 65.31 | 0.0567 | 0.2494 | 4.4 | 0.224 | 0.494 |
| _R-1233xf_R-1234yf_R-1224yd_W=_0.0156_0.0044_0.98 | 65.29 | 0.0566 | 0.2492 | 4.399 | 0.206 | 0.454 |
| _R-1233xf_R-1234yf_R-1224yd_W=_0.016_0.004_0.98 | 65.27 | 0.0566 | 0.2489 | 4.398 | 0.188 | 0.413 |
| _R-1233xf_R-1234yf_R-1224yd_W=_0.0164_0.0036_0.98 | 65.25 | 0.0566 | 0.2487 | 4.397 | 0.17 | 0.372 |
| _R-1233xf_R-1234yf_R-1224yd_W=_0.0168_0.0032_0.98 | 65.23 | 0.0565 | 0.2484 | 4.395 | 0.152 | 0.332 |
| _R-1233xf_R-1234yf_R-1224yd_W=_0.0172_0.0028_0.98 | 65.22 | 0.0565 | 0.2481 | 4.394 | 0.134 | 0.291 |
| _R-1233xf_R-1234yf_R-1224yd_W=_0.0176_0.0024_0.98 | 65.2 | 0.0564 | 0.2479 | 4.393 | 0.116 | 0.25 |
| _R-1233xf_R-1234yf_R-1224yd_W=_0.018_0.002_0.98 | 65.18 | 0.0564 | 0.2476 | 4.392 | 0.098 | 0.209 |
| _R-1233xf_R-1234yf_R-1224yd_W=_0.0184_0.0016_0.98 | 65.16 | 0.0563 | 0.2474 | 4.391 | 0.079 | 0.168 |

TABLE 9-continued

| | | | | | | |
|---|---|---|---|---|---|---|
| _R-1233xf_R-1234yf_R-1224yd_W=_0.0188_0.0012_0.98 | 65.14 | 0.0563 | 0.2471 | 4.39 | 0.061 | 0.126 |
| _R-1233xf_R-1234yf_R-1224yd_W=_0.0192_0.0008_0.98 | 65.12 | 0.0562 | 0.2468 | 4.388 | 0.043 | 0.085 |
| _R-1233xf_R-1234yf_R-1224yd_W=_0.0196_0.0004_0.98 | 65.1 | 0.0562 | 0.2466 | 4.387 | 0.025 | 0.044 |
| _R-1233xf_R-1234yf_R-1224yd_W=_0.02_0.0_0.98 | 65.08 | 0.0562 | 0.2463 | 4.386 | 0.007 | 0.002 |

| Example 9 - fluid | average glide (K) | CAP_c (kJ/m^3) | COP_c | Q_c (kJ/kg) | CAP_h (kJ/m^3) | COP_h | Q_h (kJ/kg) |
|---|---|---|---|---|---|---|---|
| _R-1233xf_R-1234yf_R-1224yd_W=_0.0_0.02_0.98 | 1.441 | 533.5 | 4.106 | 145.37 | 663.5 | 5.106 | 180.78 |
| _R-1233xf_R-1234yf_R-1224yd_W=_0.0004_0.0196_0.98 | 1.413 | 533.1 | 4.107 | 145.36 | 662.9 | 5.107 | 180.76 |
| _R-1233xf_R-1234yf_R-1224yd_W=_0.0008_0.0192_0.98 | 1.385 | 532.7 | 4.107 | 145.35 | 662.4 | 5.107 | 180.73 |
| _R-1233xf_R-1234yf_R-1224yd_W=_0.0012_0.0188_0.98 | 1.358 | 532.2 | 4.108 | 145.33 | 661.8 | 5.108 | 180.71 |
| _R-1233xf_R-1234yf_R-1224yd_W=_0.0016_0.0184_0.98 | 1.33 | 531.8 | 4.108 | 145.32 | 661.3 | 5.108 | 180.69 |
| _R-1233xf_R-1234yf_R-1224yd_W=_0.002_0.018_0.98 | 1.302 | 531.4 | 4.109 | 145.3 | 660.7 | 5.109 | 180.67 |
| _R-1233xf_R-1234yf_R-1224yd_W=_0.0024_0.0176_0.98 | 1.274 | 531 | 4.109 | 145.29 | 660.2 | 5.109 | 180.64 |
| _R-1233xf_R-1234yf_R-1224yd_W=_0.0028_0.0172_0.98 | 1.246 | 530.5 | 4.11 | 145.27 | 659.6 | 5.11 | 180.62 |
| _R-1233xf_R-1234yf_R-1224yd_W=_0.0032_0.0168_0.98 | 1.218 | 530.1 | 4.11 | 145.26 | 659.1 | 5.11 | 180.6 |
| _R-1233xf_R-1234yf_R-1224yd_W=_0.0036_0.0164_0.98 | 1.19 | 529.7 | 4.111 | 145.24 | 658.6 | 5.111 | 180.58 |
| _R-1233xf_R-1234yf_R-1224yd_W=_0.004_0.016_0.98 | 1.162 | 529.3 | 4.111 | 145.23 | 658 | 5.111 | 180.55 |
| _R-1233xf_R-1234yf_R-1224yd_W=_0.0044_0.0156_0.98 | 1.134 | 528.8 | 4.112 | 145.21 | 657.5 | 5.112 | 180.53 |
| _R-1233xf_R-1234yf_R-1224yd_W=_0.0048_0.0152_0.98 | 1.106 | 528.4 | 4.112 | 145.2 | 656.9 | 5.112 | 180.51 |
| _R-1233xf_R-1234yf_R-1224yd_W=_0.0052_0.0148_0.98 | 1.078 | 528 | 4.113 | 145.18 | 656.4 | 5.113 | 180.48 |
| _R-1233xf_R-1234yf_R-1224yd_W=_0.0056_0.0144_0.98 | 1.05 | 527.6 | 4.113 | 145.17 | 655.8 | 5.113 | 180.46 |
| _R-1233xf_R-1234yf_R-1224yd_W=_0.006_0.014_0.98 | 1.021 | 527.1 | 4.114 | 145.15 | 655.3 | 5.114 | 180.44 |
| _R-1233xf_R-1234yf_R-1224yd_W=_0.0064_0.0136_0.98 | 0.993 | 526.7 | 4.114 | 145.14 | 654.7 | 5.114 | 180.41 |
| _R-1233xf_R-1234yf_R-1224yd_W=_0.0068_0.0132_0.98 | 0.965 | 526.3 | 4.115 | 145.12 | 654.2 | 5.115 | 180.39 |
| _R-1233xf_R-1234yf_R-1224yd_W=_0.0072_0.0128_0.98 | 0.936 | 525.9 | 4.115 | 145.11 | 653.7 | 5.115 | 180.37 |
| _R-1233xf_R-1234yf_R-1224yd_W=_0.0076_0.0124_0.98 | 0.908 | 525.5 | 4.116 | 145.09 | 653.1 | 5.116 | 180.34 |
| _R-1233xf_R-1234yf_R-1224yd_W=_0.008_0.012_0.98 | 0.879 | 525 | 4.116 | 145.08 | 652.6 | 5.116 | 180.32 |
| _R-1233xf_R-1234yf_R-1224yd_W=_0.0084_0.0116_0.98 | 0.851 | 524.6 | 4.117 | 145.06 | 652 | 5.117 | 180.3 |
| _R-1233xf_R-1234yf_R-1224yd_W=_0.0088_0.0112_0.98 | 0.822 | 524.2 | 4.118 | 145.05 | 651.5 | 5.118 | 180.27 |
| _R-1233xf_R-1234yf_R-1224yd_W=_0.0092_0.0108_0.98 | 0.794 | 523.8 | 4.118 | 145.03 | 650.9 | 5.118 | 180.25 |
| _R-1233xf_R-1234yf_R-1224yd_W=_0.0096_0.0104_0.98 | 0.765 | 523.3 | 4.119 | 145.02 | 650.4 | 5.119 | 180.23 |
| _R-1233xf_R-1234yf_R-1224yd_W=_0.01_0.01_0.98 | 0.736 | 522.9 | 4.119 | 145 | 649.9 | 5.119 | 180.2 |
| _R-1233xf_R-1234yf_R-1224yd_W=_0.0104_0.0096_0.98 | 0.708 | 522.5 | 4.12 | 144.98 | 649.3 | 5.12 | 180.18 |
| _R-1233xf_R-1234yf_R-1224yd_W=_0.0108_0.0092_0.98 | 0.679 | 522.1 | 4.12 | 144.97 | 648.8 | 5.12 | 180.15 |
| _R-1233xf_R-1234yf_R-1224yd_W=_0.0112_0.0088_0.98 | 0.65 | 521.7 | 4.121 | 144.95 | 648.2 | 5.121 | 180.13 |
| _R-1233xf_R-1234yf_R-1224yd_W=_0.0116_0.0084_0.98 | 0.621 | 521.2 | 4.121 | 144.94 | 647.7 | 5.121 | 180.1 |
| _R-1233xf_R-1234yf_R-1224yd_W=_0.012_0.008_0.98 | 0.592 | 520.8 | 4.122 | 144.92 | 647.2 | 5.122 | 180.08 |
| _R-1233xf_R-1234yf_R-1224yd_W=_0.0124_0.0076_0.98 | 0.563 | 520.4 | 4.123 | 144.91 | 646.6 | 5.123 | 180.06 |
| _R-1233xf_R-1234yf_R-1224yd_W=_0.0128_0.0072_0.98 | 0.534 | 520 | 4.123 | 144.89 | 646.1 | 5.123 | 180.03 |

TABLE 9-continued

| | | | | | | | |
|---|---|---|---|---|---|---|---|
| _R-1233xf_R-1234yf_R-1224yd_W=_0.0132_0.0068_0.98 | 0.505 | 519.6 | 4.124 | 144.87 | 645.5 | 5.124 | 180.01 |
| _R-1233xf_R-1234yf_R-1224yd_W=_0.0136_0.0064_0.98 | 0.476 | 519.1 | 4.124 | 144.86 | 645 | 5.124 | 179.98 |
| _R-1233xf_R-1234yf_R-1224yd_W=_0.014_0.006 0.98 | 0.447 | 518.7 | 4.125 | 144.84 | 644.5 | 5.125 | 179.96 |
| _R-1233xf_R-1234yf_R-1224yd_W=_0.0144_0.0056_0.98 | 0.418 | 518.3 | 4.126 | 144.83 | 643.9 | 5.126 | 179.93 |
| _R-1233xf_R-1234yf_R-1224yd_W=_0.0148_0.0052_0.98 | 0.388 | 517.9 | 4.126 | 144.81 | 643.4 | 5.126 | 179.91 |
| _R-1233xf_R-1234yf_R-1224yd_W=_0.0152_0.0048_0.98 | 0.359 | 517.5 | 4.127 | 144.79 | 642.8 | 5.127 | 179.88 |
| _R-1233xf_R-1234yf_R-1224yd_W=_0.0156_0.0044_0.98 | 0.33 | 517 | 4.127 | 144.78 | 642.3 | 5.127 | 179.86 |
| _R-1233xf_R-1234yf_R-1224yd_W=_0.016_0.004_0.98 | 0.301 | 516.6 | 4.128 | 144.76 | 641.8 | 5.128 | 179.83 |
| _R-1233xf_R-1234yf_R-1224yd_W=_0.0164_0.0036_0.98 | 0.271 | 516.2 | 4.129 | 144.75 | 641.2 | 5.129 | 179.81 |
| _R-1233xf_R-1234yf_R-1224yd_W=_0.0168_0.0032_0.98 | 0.242 | 515.8 | 4.129 | 144.73 | 640.7 | 5.129 | 179.78 |
| _R-1233xf_R-1234yf_R-1224yd_W=_0.0172_0.0028_0.98 | 0.212 | 515.4 | 4.13 | 144.71 | 640.2 | 5.13 | 179.75 |
| _R-1233xf_R-1234yf_R-1224yd_W=_0.0176_0.0024_0.98 | 0.183 | 515 | 4.13 | 144.7 | 639.6 | 5.13 | 179.73 |
| _R-1233xf_R-1234yf_R-1224yd_W=_0.018_0.002_0.98 | 0.153 | 514.5 | 4.131 | 144.68 | 639.1 | 5.131 | 179.7 |
| _R-1233xf_R-1234yf_R-1224yd_W=_0.0184_0.0016_0.98 | 0.124 | 514.1 | 4.132 | 144.66 | 638.6 | 5.132 | 179.68 |
| _R-1233xf_R-1234yf_R-1224yd_W=_0.0188_0.0012_0.98 | 0.094 | 513.7 | 4.132 | 144.65 | 638 | 5.132 | 179.65 |
| _R-1233xf_R-1234yf_R-1224yd_W=_0.0192_0.0008_0.98 | 0.064 | 513.3 | 4.133 | 144.63 | 637.5 | 5.133 | 179.63 |
| _R-1233xf_R-1234yf_R-1224yd_W=_0.0196_0.0004_0.98 | 0.034 | 512.9 | 4.134 | 144.61 | 636.9 | 5.134 | 179.6 |
| _R-1233xf_R-1234yf_R-1224yd_W=_0.02_0.0_0.98 | 0.005 | 512.5 | 4.134 | 144.6 | 636.4 | 5.134 | 179.57 |

Example 10: 98 wt % of R-1224yd and Additional Compounds R-1233xf and R-1243zf

Table 10 illustrates that all blends in this Example have greater capacities and smaller COPs than neat R-1224yd. When the amount of Additional Compound ranges from pure R-1233xf to pure R-1243zf, CAP decreases and COP increases as the R-1233xf content increases from 0 to 2 wt-%. When the Additional Compound is R-1233xf (98% R-1224yd and 2% R-1233xf), the COP is the same as R-1224yd and the CAP is greater

TABLE 10

| Example 10 - fluid | T_discharge (° C.) | P_suction (MPa) | P_discharge (MPa) | compression ratio | evaporator glide (K) | condenser glide (K) |
|---|---|---|---|---|---|---|
| _R-1243zf_R-1233xf_R-1224yd_W=_0.0_0.02_0.98 | 65.08 | 0.0562 | 0.2463 | 4.386 | 0.007 | 0.002 |
| _R-1243zf_R-1233xf_R-1224yd_W=_0.0004_0.0196_0.98 | 65.1 | 0.0562 | 0.2466 | 4.387 | 0.025 | 0.039 |
| _R-1243zf_R-1233xf_R-1224yd_W=_0.0008_0.0192_0.98 | 65.12 | 0.0563 | 0.2468 | 4.388 | 0.044 | 0.076 |
| _R-1243zf_R-1233xf_R-1224yd_W=_0.0012_0.0188_0.98 | 65.14 | 0.0563 | 0.2471 | 4.389 | 0.062 | 0.113 |
| _R-1243zf_R-1233xf_R-1224yd_W=_0.0016_0.0184_0.98 | 65.16 | 0.0564 | 0.2473 | 4.389 | 0.08 | 0.15 |
| _R-1243zf_R-1233xf_R-1224yd_W=_0.002_0.018_0.98 | 65.18 | 0.0564 | 0.2476 | 4.39 | 0.099 | 0.187 |
| _R-1243zf_R-1233xf_R-1224yd_W=_0.0024_0.0176_0.98 | 65.2 | 0.0564 | 0.2479 | 4.391 | 0.117 | 0.224 |
| _R-1243zf_R-1233xf_R-1224yd_W=_0.0028_0.0172_0.98 | 65.22 | 0.0565 | 0.2481 | 4.392 | 0.135 | 0.261 |
| _R-1243zf_R-1233xf_R-1224yd_W=_0.0032_0.0168_0.98 | 65.24 | 0.0565 | 0.2484 | 4.393 | 0.154 | 0.298 |
| _R-1243zf_R-1233xf_R-1224yd_W=_0.0036_0.0164_0.98 | 65.26 | 0.0566 | 0.2486 | 4.393 | 0.172 | 0.334 |
| _R-1243zf_R-1233xf_R-1224yd_W=_0.004_0.016_0.98 | 65.28 | 0.0566 | 0.2489 | 4.394 | 0.19 | 0.371 |
| _R-1243zf_R-1233xf_R-1224yd_W=_0.0044_0.0156_0.98 | 65.3 | 0.0567 | 0.2491 | 4.395 | 0.209 | 0.407 |
| _R-1243zf_R-1233xf_R-1224yd_W=_0.0048_0.0152_0.98 | 65.32 | 0.0567 | 0.2494 | 4.396 | 0.227 | 0.443 |

TABLE 10-continued

| | | | | | | |
|---|---|---|---|---|---|---|
| _R-1243zf_R-1233xf_R-1224yd_W=_0.0052_0.0148_0.98 | 65.34 | 0.0568 | 0.2496 | 4.396 | 0.245 | 0.48 |
| _R-1243zf_R-1233xf_R-1224yd_W=_0.0056_0.0144_0.98 | 65.36 | 0.0568 | 0.2499 | 4.397 | 0.264 | 0.516 |
| _R-1243zf_R-1233xf_R-1224yd_W=_0.006_0.014_0.98 | 65.38 | 0.0569 | 0.2502 | 4.398 | 0.282 | 0.552 |
| _R-1243zf_R-1233xf_R-1224yd_W=_0.0064_0.0136_0.98 | 65.4 | 0.0569 | 0.2504 | 4.399 | 0.3 | 0.588 |
| _R-1243zf_R-1233xf_R-1224yd_W=_0.0068_0.0132_0.98 | 65.42 | 0.057 | 0.2507 | 4.399 | 0.319 | 0.624 |
| _R-1243zf_R-1233xf_R-1224yd_W=_0.0072_0.0128_0.98 | 65.44 | 0.057 | 0.2509 | 4.4 | 0.337 | 0.66 |
| _R-1243zf_R-1233xf_R-1224yd_W=_0.0076_0.0124_0.98 | 65.46 | 0.0571 | 0.2512 | 4.401 | 0.356 | 0.696 |
| _R-1243zf_R-1233xf_R-1224yd_W=_0.008_0.012_0.98 | 65.48 | 0.0571 | 0.2514 | 4.402 | 0.374 | 0.731 |
| _R-1243zf_R-1233xf_R-1224yd_W=_0.0084_0.0116_0.98 | 65.5 | 0.0572 | 0.2517 | 4.402 | 0.392 | 0.767 |
| _R-1243zf_R-1233xf_R-1224yd_W=_0.0088_0.0112_0.98 | 65.51 | 0.0572 | 0.2519 | 4.403 | 0.411 | 0.802 |
| _R-1243zf_R-1233xf_R-1224yd_W=_0.0092_0.0108_0.98 | 65.53 | 0.0573 | 0.2522 | 4.404 | 0.429 | 0.838 |
| _R-1243zf_R-1233xf_R-1224yd_W=_0.0096_0.0104_0.98 | 65.55 | 0.0573 | 0.2525 | 4.404 | 0.447 | 0.873 |
| _R-1243zf_R-1233xf_R-1224yd_W=_0.01_0.01_0.98 | 65.57 | 0.0574 | 0.2527 | 4.405 | 0.465 | 0.908 |
| _R-1243zf_R-1233xf_R-1224yd_W=_0.0104_0.0096_0.98 | 65.59 | 0.0574 | 0.253 | 4.406 | 0.484 | 0.943 |
| _R-1243zf_R-1233xf_R-1224yd_W=_0.0108_0.0092_0.98 | 65.61 | 0.0575 | 0.2532 | 4.406 | 0.502 | 0.978 |
| _R-1243zf_R-1233xf_R-1224yd_W=_0.0112_0.0088_0.98 | 65.63 | 0.0575 | 0.2535 | 4.407 | 0.52 | 1.013 |
| _R-1243zf_R-1233xf_R-1224yd_W=_0.0116_0.0084_0.98 | 65.65 | 0.0576 | 0.2537 | 4.408 | 0.539 | 1.048 |
| _R-1243zf_R-1233xf_R-1224yd_W=_0.012_0.008_0.98 | 65.67 | 0.0576 | 0.254 | 4.408 | 0.557 | 1.082 |
| _R-1243zf_R-1233xf_R-1224yd_W=_0.0124_0.0076_0.98 | 65.69 | 0.0577 | 0.2542 | 4.409 | 0.575 | 1.117 |
| _R-1243zf_R-1233xf_R-1224yd_W=_0.0128_0.0072_0.98 | 65.7 | 0.0577 | 0.2545 | 4.41 | 0.594 | 1.151 |
| _R-1243zf_R-1233xf_R-1224yd_W=_0.0132_0.0068_0.98 | 65.72 | 0.0578 | 0.2547 | 4.41 | 0.612 | 1.186 |
| _R-1243zf_R-1233xf_R-1224yd_W=_0.0136_0.0064_0.98 | 65.74 | 0.0578 | 0.255 | 4.411 | 0.63 | 1.22 |
| _R-1243zf_R-1233xf_R-1224yd_W=_0.014_0.006_0.98 | 65.76 | 0.0579 | 0.2552 | 4.411 | 0.648 | 1.254 |
| _R-1243zf_R-1233xf_R-1224yd_W=_0.0144_0.0056_0.98 | 65.78 | 0.0579 | 0.2555 | 4.412 | 0.667 | 1.289 |
| _R-1243zf_R-1233xf_R-1224yd_W=_0.0148_0.0052_0.98 | 65.8 | 0.058 | 0.2557 | 4.413 | 0.685 | 1.323 |
| _R-1243zf_R-1233xf_R-1224yd_W=_0.0152_0.0048_0.98 | 65.82 | 0.058 | 0.256 | 4.413 | 0.703 | 1.356 |
| _R-1243zf_R-1233xf_R-1224yd_W=_0.0156_0.0044_0.98 | 65.83 | 0.0581 | 0.2562 | 4.414 | 0.721 | 1.39 |
| _R-1243zf_R-1233xf_R-1224yd_W=_0.016_0.004_0.98 | 65.85 | 0.0581 | 0.2565 | 4.414 | 0.739 | 1.424 |
| _R-1243zf_R-1233xf_R-1224yd_W=_0.0164_0.0036_0.98 | 65.87 | 0.0582 | 0.2567 | 4.415 | 0.758 | 1.458 |
| _R-1243zf_R-1233xf_R-1224yd_W=_0.0168_0.0032_0.98 | 65.89 | 0.0582 | 0.257 | 4.416 | 0.776 | 1.491 |
| _R-1243zf_R-1233xf_R-1224yd_W=_0.0172_0.0028_0.98 | 65.91 | 0.0583 | 0.2573 | 4.416 | 0.794 | 1.525 |
| _R-1243zf_R-1233xf_R-1224yd_W=_0.0176_0.0024_0.98 | 65.92 | 0.0583 | 0.2575 | 4.417 | 0.812 | 1.558 |
| _R-1243zf_R-1233xf_R-1224yd_W=_0.018_0.002_0.98 | 65.94 | 0.0584 | 0.2578 | 4.417 | 0.83 | 1.591 |
| _R-1243zf_R-1233xf_R-1224yd_W=_0.0184_0.0016_0.98 | 65.96 | 0.0584 | 0.258 | 4.418 | 0.848 | 1.624 |
| _R-1243zf_R-1233xf_R-1224yd_W=_0.0188_0.0012_0.98 | 65.98 | 0.0584 | 0.2583 | 4.418 | 0.866 | 1.657 |
| _R-1243zf_R-1233xf_R-1224yd_W=_0.0192_0.0008_0.98 | 66 | 0.0585 | 0.2585 | 4.419 | 0.885 | 1.69 |
| _R-1243zf_R-1233xf_R-1224yd_W=_0.0196_0.0004_0.98 | 66.01 | 0.0585 | 0.2588 | 4.42 | 0.903 | 1.723 |
| _R-1243zf_R-1233xf_R-1224yd_W=_0.02_0.0_0.98 | 66.03 | 0.0586 | 0.259 | 4.42 | 0.921 | 1.756 |

TABLE 10-continued

| Example 10 - fluid | average glide (K) | CAP_c (kJ/m^3) | COP_c | Q_c (kJ/kg) | CAP_h (kJ/m^3) | COP_h | Q_h (kJ/kg) |
|---|---|---|---|---|---|---|---|
| _R-1243zf_R-1233xf_R-1224yd_W=_0.0_0.02_0.98 | 0.005 | 512.5 | 4.134 | 144.6 | 636.4 | 5.134 | 179.57 |
| _R-1243zf_R-1233xf_R-1224yd_W=_0.0004_0.0196_0.98 | 0.032 | 512.9 | 4.134 | 144.63 | 637 | 5.134 | 179.61 |
| _R-1243zf_R-1233xf_R-1224yd_W=_0.0008_0.0192_0.98 | 0.06 | 513.3 | 4.133 | 144.65 | 637.5 | 5.133 | 179.65 |
| _R-1243zf_R-1233xf_R-1224yd_W=_0.0012_0.0188_0.98 | 0.088 | 513.8 | 4.133 | 144.68 | 638.1 | 5.133 | 179.69 |
| _R-1243zf_R-1233xf_R-1224yd_W=_0.0016_0.0184_0.98 | 0.115 | 514.2 | 4.132 | 144.71 | 638.7 | 5.132 | 179.73 |
| _R-1243zf_R-1233xf_R-1224yd_W=_0.002_0.018_0.98 | 0.143 | 514.7 | 4.132 | 144.74 | 639.2 | 5.132 | 179.77 |
| _R-1243zf_R-1233xf_R-1224yd_W=_0.0024_0.0176_0.98 | 0.171 | 515.1 | 4.131 | 144.76 | 639.8 | 5.131 | 179.81 |
| _R-1243zf_R-1233xf_R-1224yd_W=_0.0028_0.0172_0.98 | 0.198 | 515.5 | 4.131 | 144.79 | 640.3 | 5.131 | 179.84 |
| _R-1243zf_R-1233xf_R-1224yd_W=_0.0032_0.0168_0.98 | 0.226 | 516 | 4.13 | 144.82 | 640.9 | 5.13 | 179.88 |
| _R-1243zf_R-1233xf_R-1224yd_W=_0.0036_0.0164_0.98 | 0.253 | 516.4 | 4.13 | 144.85 | 641.5 | 5.13 | 179.92 |
| _R-1243zf_R-1233xf_R-1224yd_W=_0.004_0.016_0.98 | 0.281 | 516.9 | 4.129 | 144.87 | 642 | 5.129 | 179.96 |
| _R-1243zf_R-1233xf_R-1224yd_W=_0.0044_0.0156_0.98 | 0.308 | 517.3 | 4.129 | 144.9 | 642.6 | 5.129 | 180 |
| _R-1243zf_R-1233xf_R-1224yd_W=_0.0048_0.0152_0.98 | 0.335 | 517.7 | 4.128 | 144.93 | 643.2 | 5.128 | 180.03 |
| _R-1243zf_R-1233xf_R-1224yd_W=_0.0052_0.0148_0.98 | 0.363 | 518.2 | 4.128 | 144.96 | 643.7 | 5.128 | 180.07 |
| _R-1243zf_R-1233xf_R-1224yd_W=_0.0056_0.0144_0.98 | 0.39 | 518.6 | 4.127 | 144.98 | 644.3 | 5.127 | 180.11 |
| _R-1243zf_R-1233xf_R-1224yd_W=_0.006_0.014_0.98 | 0.417 | 519.1 | 4.127 | 145.01 | 644.9 | 5.127 | 180.15 |
| _R-1243zf_R-1233xf_R-1224yd_W=_0.0064_0.0136_0.98 | 0.444 | 519.5 | 4.127 | 145.04 | 645.4 | 5.127 | 180.19 |
| _R-1243zf_R-1233xf_R-1224yd_W=_0.0068_0.0132_0.98 | 0.471 | 520 | 4.126 | 145.07 | 646 | 5.126 | 180.22 |
| _R-1243zf_R-1233xf_R-1224yd_W=_0.0072_0.0128_0.98 | 0.498 | 520.4 | 4.126 | 145.09 | 646.6 | 5.126 | 180.26 |
| _R-1243zf_R-1233xf_R-1224yd_W=_0.0076_0.0124_0.98 | 0.526 | 520.9 | 4.125 | 145.12 | 647.1 | 5.125 | 180.3 |
| _R-1243zf_R-1233xf_R-1224yd_W=_0.008_0.012_0.98 | 0.553 | 521.3 | 4.125 | 145.15 | 647.7 | 5.125 | 180.34 |
| _R-1243zf_R-1233xf_R-1224yd_W=_0.0084_0.0116_0.98 | 0.579 | 521.7 | 4.124 | 145.17 | 648.2 | 5.124 | 180.37 |
| _R-1243zf_R-1233xf_R-1224yd_W=_0.0088_0.0112_0.98 | 0.606 | 522.2 | 4.124 | 145.2 | 648.8 | 5.124 | 180.41 |
| _R-1243zf_R-1233xf_R-1224yd_W=_0.0092_0.0108_0.98 | 0.633 | 522.6 | 4.123 | 145.23 | 649.4 | 5.123 | 180.45 |
| _R-1243zf_R-1233xf_R-1224yd_W=_0.0096_0.0104_0.98 | 0.66 | 523.1 | 4.123 | 145.25 | 649.9 | 5.123 | 180.48 |
| _R-1243zf_R-1233xf_R-1224yd_W=_0.01_0.01_0.98 | 0.687 | 523.5 | 4.123 | 145.28 | 650.5 | 5.123 | 180.52 |
| _R-1243zf_R-1233xf_R-1224yd_W=_0.0104_0.0096_0.98 | 0.713 | 524 | 4.122 | 145.31 | 651.1 | 5.122 | 180.56 |
| _R-1243zf_R-1233xf_R-1224yd_W=_0.0108_0.0092_0.98 | 0.74 | 524.4 | 4.122 | 145.33 | 651.6 | 5.122 | 180.6 |
| _R-1243zf_R-1233xf_R-1224yd_W=_0.0112_0.0088_0.98 | 0.767 | 524.9 | 4.121 | 145.36 | 652.2 | 5.121 | 180.63 |
| _R-1243zf_R-1233xf_R-1224yd_W=_0.0116_0.0084_0.98 | 0.793 | 525.3 | 4.121 | 145.39 | 652.8 | 5.121 | 180.67 |
| _R-1243zf_R-1233xf_R-1224yd_W=_0.012_0.008_0.98 | 0.82 | 525.8 | 4.12 | 145.41 | 653.3 | 5.12 | 180.7 |
| _R-1243zf_R-1233xf_R-1224yd_W=_0.0124_0.0076_0.98 | 0.846 | 526.2 | 4.12 | 145.44 | 653.9 | 5.12 | 180.74 |
| _R-1243zf_R-1233xf_R-1224yd_W=_0.0128_0.0072_0.98 | 0.873 | 526.6 | 4.12 | 145.47 | 654.5 | 5.12 | 180.78 |
| _R-1243zf_R-1233xf_R-1224yd_W=_0.0132_0.0068_0.98 | 0.899 | 527.1 | 4.119 | 145.49 | 655 | 5.119 | 180.81 |
| _R-1243zf_R-1233xf_R-1224yd_W=_0.0136_0.0064_0.98 | 0.925 | 527.5 | 4.119 | 145.52 | 655.6 | 5.119 | 180.85 |
| _R-1243zf_R-1233xf_R-1224yd_W=_0.014_0.006_0.98 | 0.951 | 528 | 4.118 | 145.55 | 656.2 | 5.118 | 180.89 |
| _R-1243zf_R-1233xf_R-1224yd_W=_0.0144_0.0056_0.98 | 0.978 | 528.4 | 4.118 | 145.57 | 656.8 | 5.118 | 180.92 |
| _R-1243zf_R-1233xf_R-1224yd_W=_0.0148_0.0052_0.98 | 1.004 | 528.9 | 4.118 | 145.6 | 657.3 | 5.118 | 180.96 |

TABLE 10-continued

| | | | | | | | |
|---|---|---|---|---|---|---|---|
| _R-1243zf_R-1233xf_R-1224yd_W=_0.0152_0.0048_0.98 | 1.03 | 529.3 | 4.117 | 145.62 | 657.9 | 5.117 | 180.99 |
| _R-1243zf_R-1233xf_R-1224yd_W=_0.0156_0.0044_0.98 | 1.056 | 529.8 | 4.117 | 145.65 | 658.5 | 5.117 | 181.03 |
| _R-1243zf_R-1233xf_R-1224yd_W=_0.016_0.004_0.98 | 1.082 | 530.2 | 4.116 | 145.68 | 659 | 5.116 | 181.07 |
| _R-1243zf_R-1233xf_R-1224yd_W=_0.0164_0.0036_0.98 | 1.108 | 530.7 | 4.116 | 145.7 | 659.6 | 5.116 | 181.1 |
| _R-1243zf_R-1233xf_R-1224yd_W=_0.0168_0.0032_0.98 | 1.133 | 531.1 | 4.116 | 145.73 | 660.2 | 5.116 | 181.14 |
| _R-1243zf_R-1233xf_R-1224yd_W=_0.0172_0.0028_0.98 | 1.159 | 531.6 | 4.115 | 145.75 | 660.7 | 5.115 | 181.17 |
| _R-1243zf_R-1233xf_R-1224yd_W=_0.0176_0.0024_0.98 | 1.185 | 532 | 4.115 | 145.78 | 661.3 | 5.115 | 181.21 |
| _R-1243zf_R-1233xf_R-1224yd_W=_0.018_0.002_0.98 | 1.211 | 532.5 | 4.115 | 145.81 | 661.9 | 5.115 | 181.24 |
| _R-1243zf_R-1233xf_R-1224yd_W=_0.0184_0.0016_0.98 | 1.236 | 532.9 | 4.114 | 145.83 | 662.4 | 5.114 | 181.28 |
| _R-1243zf_R-1233xf_R-1224yd_W=_0.0188_0.0012_0.98 | 1.262 | 533.4 | 4.114 | 145.86 | 663 | 5.114 | 181.31 |
| _R-1243zf_R-1233xf_R-1224yd_W=_0.0192_0.0008_0.98 | 1.288 | 533.8 | 4.113 | 145.88 | 663.6 | 5.113 | 181.35 |
| _R-1243zf_R-1233xf_R-1224yd_W=_0.0196_0.0004_0.98 | 1.313 | 534.2 | 4.113 | 145.91 | 664.1 | 5.113 | 181.38 |
| _R-1243zf_R-1233xf_R-1224yd_W=_0.02_0.0_0.98 | 1.338 | 534.7 | 4.113 | 145.94 | 664.7 | 5.113 | 181.42 |

Example 11: 99 wt % of R-1234yf and Additional Compound R-263fb

Table 11 illustrates that as the Additional Compound content increases from 0 to 1 wt-% the COP increases and the CAP decreases.

Example 12: 99 wt % of R-1234yf and Additional Compound R-254eb

Table 12 illustrates that as the Additional Compound content increases from 0 to 1 wt-% the COP increases and the CAP decreases.

TABLE 11

| Example 11 - fluid | T_discharge (° C.) | P_suction (MPa) | P_discharge (MPa) | compression ratio | evaporator glide (K) | condenser glide (K) |
|---|---|---|---|---|---|---|
| _R-1234yf_R-236fa_W=_0.99_0.01 | 59.97 | 0.3129 | 1.0119 | 3.234 | 0.176 | 0.144 |
| _R-1234yf_R-236fa_W=_0.992_0.008 | 59.95 | 0.3135 | 1.0132 | 3.232 | 0.141 | 0.115 |
| _R-1234yf_R-236fa_W=_0.994_0.006 | 59.93 | 0.3141 | 1.0145 | 3.23 | 0.106 | 0.086 |
| _R-1234yf_R-236fa_W=_0.996_0.004 | 59.91 | 0.3147 | 1.0158 | 3.228 | 0.07 | 0.058 |
| _R-1234yf_R-236fa_W=_0.998_0.002 | 59.89 | 0.3152 | 1.0171 | 3.226 | 0.035 | 0.029 |
| _R-1234yf_R-236fa_W=_1.0_0.0 | 59.87 | 0.3158 | 1.0184 | 3.225 | 0 | 0 |

| Example 11 - fluid | average glide (K) | CAP_c (kJ/m^3) | COP_c | Q_c (kJ/kg) | CAP_h (kJ/m^3) | COP_h | Q_h (kJ/kg) |
|---|---|---|---|---|---|---|---|
| _R-1234yf_R-236fa_W=_0.99_0.01 | 0.16 | 1991 | 3.778 | 122.52 | 2518 | 4.778 | 154.96 |
| _R-1234yf_R-236fa_W=_0.992_0.008 | 0.128 | 1993.5 | 3.778 | 122.49 | 2521.2 | 4.778 | 154.91 |
| _R-1234yf_R-236fa_W=_0.994_0.006 | 0.096 | 1996 | 3.777 | 122.45 | 2524.5 | 4.777 | 154.87 |
| _R-1234yf_R-236fa_W=_0.996_0.004 | 0.064 | 1998.6 | 3.777 | 122.42 | 2527.7 | 4.777 | 154.82 |
| _R-1234yf_R-236fa_W=_0.998_0.002 | 0.032 | 2001.1 | 3.777 | 122.38 | 2530.9 | 4.777 | 154.78 |
| _R-1234yf_R-236fa_W=_1.0_0.0 | 0 | 2003.6 | 3.777 | 122.34 | 2534.1 | 4.777 | 154.74 |

TABLE 12

| Example 12 - fluid | T_discharge (° C.) | P_suction (MPa) | P_discharge (MPa) | compression ratio | evaporator glide (K) | condenser glide (K) |
|---|---|---|---|---|---|---|
| _R-1234yf_R-254eb_W=_0.99_0.01 | 60.02 | 0.3121 | 1.0094 | 3.234 | 0.217 | 0.207 |
| _R-1234yf_R-254eb_W=_0.992_0.008 | 59.99 | 0.3129 | 1.0112 | 3.232 | 0.173 | 0.166 |
| _R-1234yf_R-254eb_W=_0.994_0.006 | 59.96 | 0.3136 | 1.013 | 3.23 | 0.13 | 0.124 |
| _R-1234yf_R-254eb_W=_0.996_0.004 | 59.93 | 0.3143 | 1.0148 | 3.228 | 0.087 | 0.083 |
| _R-1234yf_R-254eb_W=_0.998_0.002 | 59.9 | 0.3151 | 1.0166 | 3.226 | 0.043 | 0.041 |
| _R-1234yf_R-254eb_W=_1.0_0.0 | 59.87 | 0.3158 | 1.0184 | 3.225 | 0 | 0 |

| Example 12 - fluid | average glide (K) | CAP_c (kJ/m^3) | COP_c | Q_c (kJ/kg) | CAP_h (kJ/m^3) | COP_h | Q_h (kJ/kg) |
|---|---|---|---|---|---|---|---|
| _R-1234yf_R-254eb_W=_0.99_0.01 | 0.212 | 1987.8 | 3.78 | 122.95 | 2513.7 | 4.78 | 155.47 |
| _R-1234yf_R-254eb_W=_0.992_0.008 | 0.17 | 1991 | 3.78 | 122.83 | 2517.7 | 4.78 | 155.32 |
| _R-1234yf_R-254eb_W=_0.994_0.006 | 0.127 | 1994.1 | 3.779 | 122.71 | 2521.8 | 4.779 | 155.18 |
| _R-1234yf_R-254eb_W=_0.996_0.004 | 0.085 | 1997.3 | 3.778 | 122.58 | 2525.9 | 4.778 | 155.03 |
| _R-1234yf_R-254eb_W=_0.998_0.002 | 0.042 | 2000.4 | 3.777 | 122.46 | 2530 | 4.777 | 154.88 |
| _R-1234yf_R-254eb_W=_1.0_0.0 | 0 | 2003.6 | 3.777 | 122.34 | 2534.1 | 4.777 | 154.74 |

While the invention has been described with reference to one or more embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. In addition, all numerical values identified in the detailed description shall be interpreted as though the precise and approximate values are both expressly identified.

What is claimed is:

1. A composition comprising:
   (a) -1-chloro-2,3,3,3-tetrafluoropropene (1224 yd),
   (b) at least one of 2,3,3,3-tetrafluoropropene (1234yf) and 1-chloro-trifluoropropyne,
   (c) optionally 1,2-dichloro-3,3,3-trifluoropropene (1223xd), and
   (d) at least one additional compound selected from 2-chloro-3,3,3-trifluoropropene (1233xf), 3,3,3-trifluoropropene (1243zf), 2-chloro-1,1,1,2 tetrafluoropropane (244bb), 2-bromo-3,3,3-trifluoropropene (1233xfB), 2,3-dichloro-1,1,1-trifluoropropane (243 db), 3,3,3-trifluoropropyne, 1-chloro-1,2,3,3,3-pentafluoropropene (1215yb), 2-chloro-1,3,3,3-tetrafluoropropene (1224xe), 3-chloro-1,1,1-trifluoropropane (253fb), 1,1,1,2-tetrafluoropropane (254eb), 1,1-dichloro-2,3,3,3-trifluoroprop-1-ene (1214ya), 2,2-dichloro-1,1,1-trifluoroethane (123), and 2-chloro-1,1,1,2-tetrafluoroethane (124),
   wherein the amount of 1-chloro-2,3,3,3-tetrafluoropropene (1224 yd) is greater than the amount of the at least 2,3,3,3-tetrafluoropropene (1234yf) and 1-chloro-trifluoropropyne, optional 1,2-dichloro-3,3,3-trifluoropropene (1223xd), and the at least one additional compound.

2. The composition of claim 1 wherein the amount of the at least one of 2,3,3,3-tetrafluoropropene (1234yf) and 1-chloro-trifluoropropyne, optional 1,2-dichloro-3,3,3-trifluoropropene (1223xd), and the at least one additional compound ranges from greater than 0 to about 8% by weight based on the total amount of the composition.

3. The composition of claim 1 wherein 1-chloro-trifluoropropyne is present.

4. The composition of claim 1, comprising between greater than 0 and about 10 wt % 1,2-dichloro-3,3,3-trifluoropropene (1223xd) based on the total amount of the composition.

5. The composition of claim 1 wherein 2,3,3,3-tetrafluoropropene (1234yf) is present in an amount of between >0 and less than about 0.02% by weight, based on the total amount of the composition.

6. The composition of claim 1 wherein 2,3-dichloro-1,1,1-trifluoropropane (243 db) is present.

7. A composition comprising 1-chloro-2,3,3,3-tetrafluoropropene (1224 yd), 1-chloro-trifluoropropyne, and at least one additional compound selected from the group consisting of 2-chloro-3,3,3-trifluoropropene (1233xf), 2,3,3,3-tetrafluoropropene (1234yf), 3,3,3-trifluoropropene (1243zf), 2-chloro-1,1,1,2 tetrafluoropropane (244bb), (2-bromo-3,3,3-trifluoropropene (1233xfB), 2,3-dichloro-1,1,1-trifluoropropane (243 db), 3,3,3-trifluoropropyne, 1-chloro-1,2,3,3,3-pentafluoropropene (1215yb), 1,2-dichloro-3,3,3-trifluoropropene (1223xd), 2-chloro-1,3,3,3-tetrafluoropropene (1224xe), 3-chloro-1,1,1-trifluoropropane (253fb), 1,1-dichloro-2,3,3,3-trifluoroprop-1-ene (1214ya), 2,2-dichloro-1,1,1-trifluoroethane (123), and 2-chloro-1,1,1,2-tetrafluoroethane (124).

8. A composition comprising 1-chloro-2,3,3,3-tetrafluoropropene (1224 yd),
   (i) one of 1-chloro-trifluoropropyne and 1,2-dichloro-3,3,3-trifluoropropene (1223xd),
   (ii) one of 2,3,3,3-tetrafluoropropene (1234yf) and 2-chloro-3,3,3-trifluoropropene (1233xf), and
   (iii) at least one additional compound selected 2-bromo-3,3,3-trifluoropropene (1233xfB), 2,3-dichloro-1,1,1-trifluoropropane (243 db), 1-chloro-1,2,3,3,3-pentafluoropropene (1215yb), 2-chloro-1,3,3,3-tetrafluoropropene (1224xe), 3-chloro-1,1,1-trifluoropropane (253fb), 1,1,1,2 tetrafluoroprop-1-ene (254eb), 1,1-dichloro-2,3,3,3-tetrafluoroprop-1-ene (1214ya), 2,2-dichloro-1,1,1-trifluoroethane (123), and 2-chloro-1,1,1,2-tetrafluoroethane (124).

9. The composition of claim 8 wherein 2,3-dichloro-1,1,1-trifluoropropane (243 db) is present.

10. The composition of claim 8 wherein at least two of 2-bromo-3,3,3-trifluoropropene (1233xfB), 2,3-dichloro-1,1,1-trifluoropropane (243 db), 1-chloro-1,2,3,3,3-pentafluoropropene (1215yb), 2-chloro-1,3,3,3-tetrafluoropropene (1224xe), 3-chloro-1,1,1-trifluoropropane (253fb), 1,1,1,2-tetrafluoropropane (254eb), 1,1-dichloro-2,3,3,3-tetrafluoroprop-1-ene (1214ya), 2,2-dichloro-1,1,1-trifluoroethane (123), and 2-chloro-[1,1,1,2-tetrafluoroethane (124) are present.

* * * * *